June 9, 1959 E. S. BOERNER Plant Pat. 1,840
ROSE PLANT
Filed Nov. 7, 1958
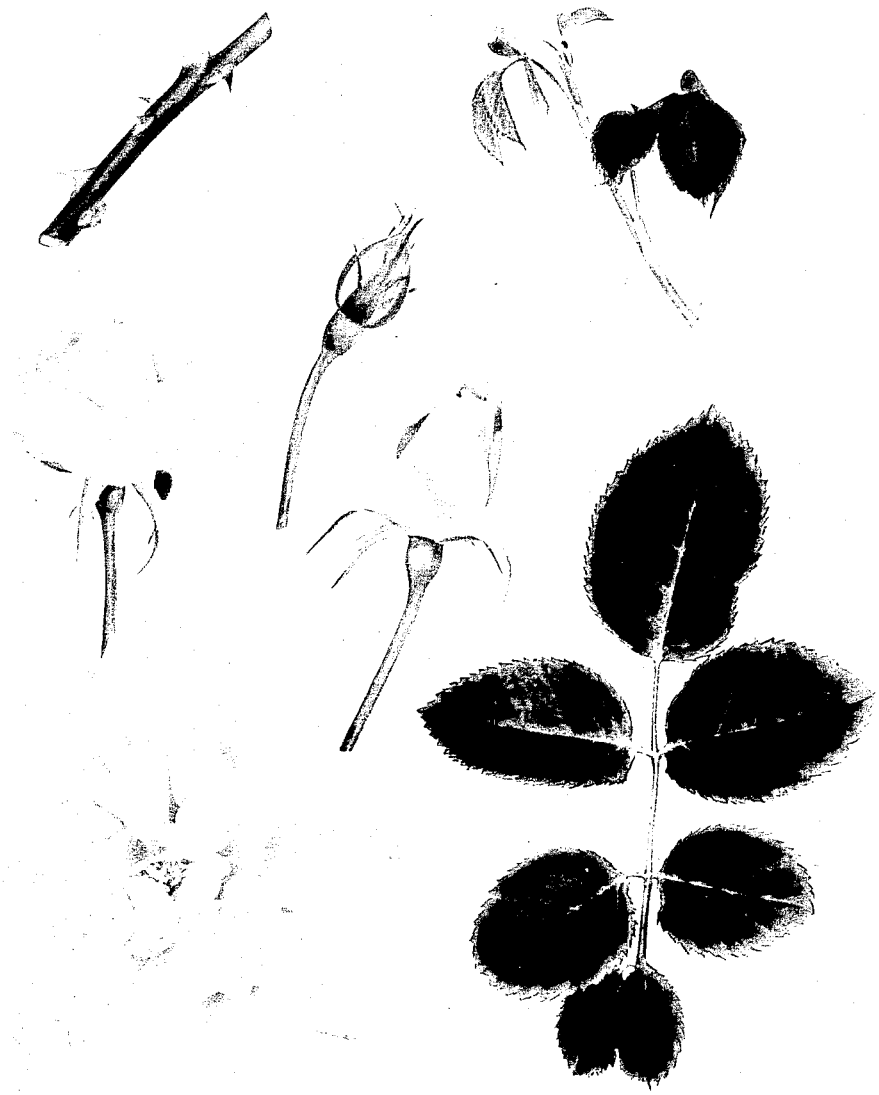
Inventor.
E. S. Boerner
By: Robb & Robb
Attorneys United States Patent Office Plant Pat. 1,840
Patented June 9, 1959

1,840

ROSE PLANT

Eugene S. Boerner, Newark, N.Y., assignor to Jackson & Perkins Company, Newark, N.Y., a corporation of New York Application November 7, 1958, Serial No. 772,642

1 Claim. (Cl. 47—61)

The present invention relates to a new and distinct variety of rose plant of the large-flowered polyantha class, which was originated by me by crossing the variety "Chic" (Plant Patent No. 1,286) with an unnamed and unpatented seedling of "Garnette" (unpatented).

The primary objective of this breeding was to produce a new rose variety that is better suited for both greenhouse forcing and outdoor garden cultivation. This objective was fully achieved, along with other desirable improvements, as evidenced by the following unique combination of characteristics which are outstanding in the new variety and distinguish it from its parents, as well as from all other varieties of which I am aware:

(1) Good qualities for both greenhouse forcing and outdoor cultivation;

(2) Ovoid form of the buds and their habit of opening very slowly;

(3) Full-open form of the mature flowers;

(4) Stiff texture of the flower petals;

(5) A distinctive general color tonality of the blooms corresponding to Rose Doree, with the lower half of the petals lightly overcast with Coral Red, said color persisting well throughout the entire normal period of good condition of the flower; and (6) Long-lasting quality of the flowers, both as cut flowers and on the plant.

Asexual reproduction of my new variety by budding, as performed at Newark, New York, and also at Pleasanton, California, shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.
*Seed parent.*—"Chic."
*Pollen parent.*—An unnamed seedling of "Garnette."
Classification:
*Botanic.*—Large-flowered polyantha.
*Commercial.*—Floribunda.

*Flower*

(Observations made from specimens grown in a greenhouse at Newark, New York, in the early afternoon in the latter part of June.)

Blooming habit: Recurrent—continuous.
Bud:
*Size.*—Medium.
*Form.*—Ovoid; is not affected by wet or hot weather.
*Color.*—When sepals first divide—Nopal Red, Plate 1. When petals begin to unfurl—Scarlet-Red, Plate 1, lightly overcast with Scarlet, Plate 1. When half-blown: inside of petals—Begonia Rose, Plate 1, lightly overcast with Scarlet, Plate 1; reverse of petals—Eosine Pink, Plate 1, with outer edge of petal lightly overcast with Scarlet-Red, Plate 1.

*Sepals.*—Branched, with "hood" above bud; curl back when petals begin to unfurl. Color: inside—Light Turtle Green, Plate 32; outside—Cress Green, Plate 31.
*Calyx.*—Color—Cress Green, Plate 31. Shape—pear. Size—small. Aspect—smooth. Odor when rubbed—none.
*Peduncle.* — Length — medium. Aspect — smooth. Strength—erect; slender. Color—Parrot Green, Plate 6.
*Opening.*—Opens up well; is not affected by adverse weather conditions.

Bloom:
*Size.*—Medium. Average size when fully expanded—3½ inches.
*Borne.*—Singly, and several together, and in irregular clusters.
*Stems.*—Medium length; strong.
*Form (when first open).*—Cupped. Permanence—retains its form to the end.
*Petalage.*—Very double (many petals and stamens hidden). Number of petals under normal conditions—from 40 to 50.
*Color.*—Center of flower—Rose Doree, Plate 1, lightly overcast with Scarlet, Plate 1. Outer petals—Rose Doree, Plate 1. Base of petals (aiglet)—Amber Yellow, Plate 16. Inside of petals—Rose Doree, Plate 1, with lower half of petals slightly overcast with Coral Red, Plate 13. Reverse of petals—Eosine Pink, Plate 1. General tonality from a distance—Rose Doree, Plate 1.
*Discoloration.*—General tonality at end of first day—Rose Doree, Plate 1, lightly overcast with Scarlet, Plate 1. Second day—Rose Doree, Plate 1, lightly overcast with Scarlet, Plate 1. Third day—Rose Doree, Plate 1, lightly overcast with Rose Red, Plate 13.

Petals:
*Texture.*—Thick; stiff; is not affected by wet or hot weather.
*Appearance.*—Inside—satiny. Outside—shiny.
*Form.*—Oval.
*Arrangement.* — Imbricated (regularly arranged shingle-like).
*Petaloids in center.*—Few; small.
*Persistence.*—Drop off cleanly.
*Fragrance.*—Strong. Nature—"Old Rose perfume" (centifolia).
*Lasting quality.*—On the plant—very long. As cut flower—very long.

*Genital organs*

Stamens, anthers: Medium size; few; regularly arranged around styles. Color—Capucine Yellow, Plate 3.
Stamens, filaments (threads): Medium length. Color—Primrose Yellow, Plate 30.
Pollen: Color—Cartridge Buff, Plate 30.
Styles: Bunched; uneven length; medium length; thin.
Stigmas: Color—Colonial Buff, Plate 30.
Ovaries: All enclosed in calyx.
Hips: None.
Seeds: None.

*Plant*

Form: Bush.
Growth: Vigorous; upright.

Foliage: Compound of 5 to 7 leaflets.

*Size.*—Medium.

*Quantity.*—Normal.

*Color.*—New foliage: upper side—Yellowish Oil Green, Plate 5, lightly overcast with Oxblood Red, Plate 1; under side—Van Dyke Red, Plate 13. Old foliage: upper side—Varley's Green, Plate 18; under side—Light Cress Green, Plate 31.

*Shape.*—Oval pointed.

*Texture.*—Upper side—glossy. Under side—smooth.

*Ribs and veins.*—Ordinary.

*Edge.*—Serrated (saw-toothed).

*Serrations.*—Both double and single; sharp.

*Leaf stem.*—Color—Absinthe Green, Plate 31. Under side—prickly.

*Stipules.*—Medium length; bearded.

Wood:

*New wood.*—Color—Lettuce Green, Plate 5. Bark—smooth.

*Old wood.*—Color—Forest Green, Plate 17. Bark—smooth.

Thorns:

*Thorns.*—Quantity: on main stalks from base— many; on laterals from stalk—many. Form—narrow base; medium length; hooked downward. Color (when young)—Cream Buff, Plate 30. Position—irregular.

*Prickles.*—Quantity: on main stalks—none; on laterals—none.

*Short needles.*—Quantity: on main stalks—none; on laterals—none.

I claim:

A new and distinct variety of rose plant of the large-flowered polyantha class, substantially as herein shown and described, characterized particularly as to novelty by the unique combination of good qualities for both greenhouse forcing and outdoor cultivation, ovoid form of the bud and habit of opening very slowly, full-open form of the mature flowers, stiff texture of the flower petals, a distinctive Rose Doree general color tonality of the flowers, with the lower half of the flower petals lightly overcast, with Coral Red, good color retention of the flowers, and long-lasting flower qualities both as cut flowers and on the plant.

No references cited.